United States Patent [19]

Sellstedt et al.

[11] 4,056,525

[45] Nov. 1, 1977

[54] 2,3-DIALKOXY-3H-1,4-BENZODIAZEPINES

[75] Inventors: John H. Sellstedt, Pottstown; Daniel M. Teller, Devon, both of Pa.

[73] Assignee: American Home Products Corporation, New York, N.Y.

[21] Appl. No.: 583,307

[22] Filed: June 2, 1975

[51] Int. Cl.$^2$ ............................................. C07D 243/24
[52] U.S. Cl. .............................. 260/239 BD; 424/244
[58] Field of Search ................................. 260/239 BD

[56] References Cited

U.S. PATENT DOCUMENTS

| 3,247,186 | 4/1966 | Reedes et al. | 260/239 BD |
| 3,523,939 | 8/1970 | Frye et al. | 260/239 BD |
| 3,681,341 | 8/1972 | Earley et al. | 260/239 BD |

FOREIGN PATENT DOCUMENTS

| 6,917,680 | 5/1970 | Netherlands | 260/239 BD |

*Primary Examiner*—Raymond V. Rush
*Attorney, Agent, or Firm*—Robert Wiser

[57] ABSTRACT

2,3-Dialkoxy-3H-1,4-benzodiazepines which have CNS depressant activity.

1 Claim, No Drawings

2,3-DIALKOXY-3H-1,4-BENZODIAZEPINES

BACKGROUND OF THE INVENTION

Netherlands Patent No. 6917680 describes inter alia 2-alkoxy-3-hydroxy-3H-1,4-benzodiazepines. The present invention concerns 2,3-dialkoxy-3H-1,4-benzodiazepines.

SUMMARY OF THE INVENTION

The invention sought to be patented in its composition aspect resides in the concept of a chemical compound of the formula:

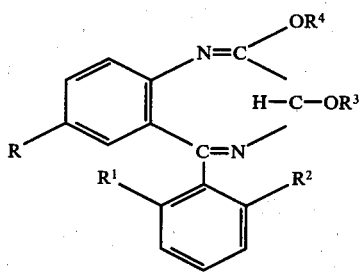

I wherein R, $R^1$ and $R^2$ are independently selected from among hydrogen, halo, trifluoromethyl, nitro, carbalkoxy, lower alkyl thio, or lower alkyl sulfonyl; and $R^3$ and $R^4$ are independently selected from among lower alkyl; and the pharmaceutically acceptable addition salts thereof.

The tangible embodiments of the composition aspect of the invention possess the inherent applied use characteristics of being anti-convulsants, of antagonizing the effects of morphine, of inducing motor, and respiratory depression, and sedation and ataxia in warm-blooded animals.

The invention sought to be patented in a first subgeneric aspect of the composition aspect of the invention resides in the concept of a compound of formula I wherein R, $R^1$, and $R^2$ are independently selected from among hydrogen and halo.

The invention sought to be patented in a second subgeneric aspect of the invention resides in the concept of a compound of formula I wherein R and $R^1$ are independently selected from among the group hydrogen and halo and $R^2$ is hydrogen.

The invention sought to be patented in a third subgeneric aspect of the principle composition aspect resides in the concept of a compound of the formula I wherein R is halo, $R^1$ is hydrogen or halo and $R^2$ is hydrogen.

The invention sought to be patented in a fourth subgeneric aspect of the composition aspect of the invention resides in the concept of a compound of the formula I wherein R is halo; and $R^1$ and $R^2$ are hydrogen.

The invention sought to be patented in a fifth subgeneric aspect of the composition aspect of the invention resides in the concept of a compound of formula I wherein R and $R^1$ are independently selected from among halo and $R^2$ is hydrogen.

DESCRIPTION OF THE PREFERRED EMBODIMENT

The compounds of formula I may be prepared from the corresponding 2-halo-3-alkoxy-3H-1,4-benzodiazepine, described in allowed U.S. Pat. No. 3,882,101, by treating them with an alcohol or an alkali metal alkoxide, at moderate temperature, conveniently room temperature, in a suitable solvent which, if liquid, is conveniently an excess of the alcohol employed as a reactant or of that used to form the alkali metal alkoxide. If desired, a co-solvent to assist the solubility of the 2-halo benzodiazepine employed may be used. Tetrahydrofuran is convenient for this purpose. Recovery, if desired, may be by standard techniques.

For example, 2,7-dichloro-5-(o-chlorophenyl)-3-methoxy-3H-1,4-benzodiazepine is treated in a mixture of tetrahydrofuran and ethanol, at room temperature with sodium ethoxide. After addition of water, the reaction mixture is partitioned with diethyl ether, and the organic phase is then dried, concentrated and the crystalline product so formed, recovered to give 7-chloro-5-(o-chlorophenyl)-2-ethoxy-2-methoxy-3H-1,4-benzodiazepine.

The central nervous system depressant activity of the tangible embodiments of the invention can be elicited by a series of pharmacological evaluation procedures well-known in the art. When administered to mice at dosage levels of 400, 127, 40, 12.7, 4.0, 1.27, 0.4, 0.127, 0.04 mg/kg. followed by observation of effect over a minimum of 2 hours, the tangible embodiments of the invention exhibit the effect of inducing general depression of the animals as evidenced by decreased spontaneous motor activity and decreased respiration loss of some reflex activity, and sedation and ataxia as determined by ease of a pole climb and an inclined screen.

For example, 7-chloro-5-(o-chlorophenyl)-2-ethoxy-3-methoxy-3H-1,4-benzodiazepine exhibits the effect of inducing decreased motor activity, decreased respiration, sedation, ataxia and loss of righting reflex at an oral dose of 1.27 mg/kg. It also exhibits the effect of causing loss of extensor reflex at an oral dose of 127 mg/kg., and protection against the effects of maximal electro shock at an oral dose of 40.0 mg/kg. The tangible embodiments when administered orally to mice inhibit the clonic and tonic convulsions and death caused by metrazole. To demonstrate this effect, the tangible embodiments are administered orally to groups of six mice, equally divided as to sex. One hour later, the animals are challenged with metrazole 125 mg/kg. i.p. The incidence of clonic and tonic convulsions and death is observed for one-half hour. Relative protection against convulsions and death is determined by comparison with controls run simultaneously. For example, 7-chloro-5-(o-chlorophenyl)-2-ethoxy-3-methoxy-3H-1,4-benzodiazepine when administered orally to mice, inhibits clonic convulsions induced by metrazole at an $ED_{50}$ of 1.05 mg/kg., inhibits tonic convulsions at an $ED_{50}$ of 0.56 mg/kg., and inhibits death at an $ED_{50}$ of 0.52 mg/kg. and an overall average $ED_{50}$ against all three effects of 0.7 mg/kg. The tangible embodiments of the invention synergize with reserpine, inducing ptosis in warm-blooded animals. To demonstrate this effect, the tangible embodiments are administered orally to groups of 6 mice, equally divided as to sex. One hour later the animals are challenged with reserpine, 2.5 mg/kg. i.p. The degree of ptosis for each eye is determined at 1 hour and 2 hours post treatment. The degree of ptosis is determined by comparison with controls run simultaneously. The tangible embodiments of the invention show little or no antagonism and some synergism to the tremors, salivation, lacrimation, and diarrhea induced in warm-blooded animals by tremorine. These effects may be demonstrated by administering the tangible embodiments at graded dose levels to groups of six mice, equally divided as to sex. One hour later, the animals are challenged with tremorine, 30 mg/kg. i.p. The animals are graded at ½ hour, 1 and 2 hours post treatment for degree of tremors, salivation, lacrimation, and diarrhea. A comparison with simultaneously run controls is used to determine the effect of the test substance on the respective conditions.

When administered orally to mice, 7-chloro-5-(o-chlorophenyl)-2-ethoxy-3-methoxy-3H-1,4-benzodiazepine antagonizes the tremors at an $ED_{50}$ of greater than 400 mg/kg., and synergizes with tremorine in inducing salivation, diarrhea, and lacrimation. The tangible embodiments of the invention exhibit the effect of inducing ataxia in warm-blooded animals. This effect may be demonstrated by a procedure described by N. W. Dunham and T. W. Heya in the Journal of the American Pharmaceutical Association, Scientific Edition, 1957, Vol. 46, page 206. In this procedure the tangible embodiments are administered at graded dose levels to groups of 6 mice, equally divided as to sex. At post treatment times of ½ hour, 1 and 2 hours, each animal is tested on the rotarod for 1 minute. The degree of ataxia induced is determined by comparison with untreated control animals. When administered orally to mice, 7-chloro-5-(o-chlorophenyl)-2-ethoxy-3-methoxy-3H-1,4-benzodiazepine induces ataxia at an $ED_{50}$ of 10.5 mg/kg. The tangible embodiments of the invention exhibit the effect of inhibiting the "Straub-tail" and circling induced in mice by morphine. To demonstrate this effect, the procedure described by Holter in Acta Pharmacologica et Toxicologica, 13, page 113, (1957), is employed. The tangible embodiments are administered at graded dose levels to groups of 6 mice, equally divided as to sex. One hour later, the animals are challenged with morphine sulfate, 100 mg/kg. i.p.

The incidence of "Straub-tail" and circling is noted and compared with controls. When administered orally to mice, 7-chloro-5-(o-chlorophenyl)-2-ethoxy-3-methoxy-3H-1,4-benzodiazepine inhibits circling at an $ED_{50}$ of .37 mg/kg. and "Straub-tail" at an $ED_{50}$ of .34 mg/kg. with an average $ED_{50}$ against both effects of 0.34 mg/kg.

The tangible embodiments of the invention exhibit a protective effect against tonic electroshock seizures. To demonstrate this effect, a procedure described by Swingard et al. in the Journal of Pharmacology, 106, page 319 (1952) is employed. The tangible embodiments are administered orally to groups of 6 mice. One hour later, the animals are given supramaximal electroshock through corneal electrodes, current strength of 25 milliamperes for 0.2 seconds.

The presence or absence of tonic extensor seizures is noted and the percent protection against these seizures is calculated. When administered to mice, 7-chloro-5-(o-chlorophenyl)-2-ethoxy-3-methoxy-3H-1,4-benzodiazepine protects against tonic seizures induced by electroshock at an $ED_{50}$ of 23 mg/kg.

As used herein, the term lower alkyl means a saturated hydrocarbon radical including the straight and branched chain radicals of from 1 to 6 carbon atoms, among which are for the purposes of illustration, but without limiting the generality of the foregoing, methyl, ethyl, and i-butyl. The term halo means fluoro, chloro or bromo. The term carbalkoxy means a radical of the formula

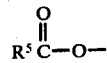

wherein $R^5$ is lower alkyl of from 1 to 5 carbon atoms.

The following example further illustrates the best mode contemplated by the inventors for the practice of their invention.

EXAMPLE

7-Chloro-5-(o-Chlorophenyl)-2-Ethoxy-3-Methoxy-3H-1,4-Benzodiazepine

To a solution of 5.40 g. (0.015 mol) of 2,7-dichloro-5-(o-chlorophenyl)-3-methoxy-3H-1,4-benzodiazepine in 25 ml. of THF is added a solution of NaOEt [from 0.34 g. (0.015 ml.) of Na] in 20 ml. of EtOH. The mixture is stirred for 2½ hour at room temperature, poured into 500 ml. of ice water, and extracted twice with $Et_2O$. The extracts are washed with saturated $NaHCO_3$ and brine and dried. Concentration and crystallization gives 3 g. of the title compound; m.p. 110°–113°.

Analysis for: $C_{18}H_{16}Cl_2N_2O_2$,

Calculated: C, 59.52; H, 4.44; N, 7.72; Cl, 19.52,

Found: C, 59.41; H, 4.23; N, 7.60; Cl, 19.53.

The subject matter which the applicants regard as their invention is particularly pointed out and distinctly claimed as follows:

1. 7-chloro-5-(o-chlorophenyl)-2-ethoxy-3-methoxy-3H-1,4-benzodiazepine.

* * * * *